United States Patent
Chen et al.

(10) Patent No.: US 8,058,236 B2
(45) Date of Patent: Nov. 15, 2011

(54) AQUEOUS INHALATION PHARMACEUTICAL COMPOSITION

(75) Inventors: Pao-Nien Chen, Shi Chi (TW);
Shyh-Fong Chen, Shi Chi (TW);
Shu-Chien Liu, Shi Chi (TW);
Fan-Jung Liu, Shi Chi (TW)

(73) Assignee: Development Center for Biotechnology, Shi Chi (TW)

( * ) Notice: Subject to any disclaimer, the term of this patent is extended or adjusted under 35 U.S.C. 154(b) by 0 days.

(21) Appl. No.: 11/440,775

(22) Filed: May 25, 2006

(65) Prior Publication Data

US 2007/0140976 A1 Jun. 21, 2007

(30) Foreign Application Priority Data

Dec. 15, 2005 (TW) .................................. 094144473

(51) Int. Cl.
*A61K 38/28* (2006.01)
*C07K 14/62* (2006.01)

(52) U.S. Cl. ....................................................... 514/5.9
(58) Field of Classification Search .................. None
See application file for complete search history.

(56) References Cited

U.S. PATENT DOCUMENTS

| 5,997,848 | A | 12/1999 | Patton et al. |
| 6,375,975 | B1 * | 4/2002 | Modi ............................ 424/434 |
| 6,702,997 | B2 * | 3/2004 | Chaudry et al. ................ 424/45 |
| 2003/0198602 | A1 | 10/2003 | Chen et al. |

FOREIGN PATENT DOCUMENTS

| EP | 0845265 | 6/1998 |
| JP | 06507904 T | 9/1994 |
| JP | 08512027 T | 12/1996 |
| JP | 10510827 T | 10/1998 |
| JP | 11292787 A | 10/1999 |
| JP | 2003-519175 T | 6/2003 |
| JP | 2004-532861 T | 10/2004 |
| WO | 9221017 A1 | 11/1992 |
| WO | 9500127 A1 | 1/1995 |
| WO | 9619197 A1 | 6/1996 |
| WO | 0149274 A2 | 7/2001 |
| WO | 02094342 A2 | 11/2002 |

OTHER PUBLICATIONS

Ngo et al., in the Protein Folding Problem and Tertiary Structure Prediction, 1994, Merz et al. (ed.), Birkhauser, Boston, MA, pp. 433 and 492-495.*
Hagerman et al., Expert Opinion on Drug Delivery, Jan. 2006, vol. 3, No. 1, pp. 71-86.*
Mollmann et al. (Pharmaceutical Research, vol. 22, No. 11, Nov. 2005).*
Weber et al. (Pediatric Pulmonology 23: 249-260, 1997).*
Sodium dodecyl sulfate, [online], retrived from <URL: http://en.wikipedia.org/wiki/Sodium_lauryl_sulfate>, retrieved the Internet on May 22, 2007.*
Shao et al., "Bile Salt-Fatty Acid Mixed Micelles as Nasal Absorption Promotors. III. Effects on Nasal Transport and Enzymatic Degradation of Acyclovir Prodrugs", Pharmaceutical Research, vol. 11, No. 2, pp. 243-250, 1994 Plenum Publishing Corporation.
Patton et al., "Clinical Pharmacokinetics and Pharmacodynamics of Inhaled Insulin", Clinical Pharmacokinetic, vol. 43, No. 12, pp. 781-801, 2004 Adis Data Information BV.
Pontiroli et al., "Intranasal Drug Delivery Potential Advantages and Limitations from a Clinical Pharmacokinetic Perspective", Clinical Pharrnacokinet, vol. 17, No. 5, pp. 299-307 1989.

* cited by examiner

*Primary Examiner* — Suzanne M Noakes
*Assistant Examiner* — Jae W Lee
(74) *Attorney, Agent, or Firm* — Lerner, David, Littenberg, Krumholz & Mentlik, LLP

(57) ABSTRACT

An aqueous inhalation pharmaceutical composition comprising a polypeptide or protein is provided. The composition of the present invention can improve the bioavailability of the polypeptide and protein, and avoid inducing toxicity in the lung.

10 Claims, 1 Drawing Sheet

AQUEOUS INHALATION PHARMACEUTICAL COMPOSITION

FIELD OF THE INVENTION

The invention relates to an aqueous inhalation pharmaceutical composition comprising a polypeptide or protein. The composition of the present invention can improve the bioavailability of the polypeptide and protein, and reduce the toxicity in the lung.

BACKGROUND OF THE INVENTION

It is found that most orally administered polypeptide and protein (such as insulin) drugs cannot be well absorbed for the reasons that the polypeptides and proteins contained therein are readily decomposed in the stomach, and/or cannot penetrate the intestinal mucosa cells due to their large molecular size and their hydrophilic property. Even if the polypeptides and proteins can be absorbed, they can hardly avoid the first-pass effect in the liver. Therefore, the bioavailability of all polypeptide and protein drugs is too low (<2%) to achieve a good therapeutic effect (A. E. Pontiroli et al., Clin. Pharmacokinet., 17(5): 299-307, 1989). In view of the above, polypeptide and protein drugs are generally administered by injection. However, this administration manner brings the patients, who need a long-term treatment, a lot of agony so as to seriously affect their compliance. Thus, non-oral administration routes, such as nasal, buccal, anal, ocular, and pulmonary administrations, have been developed.

Since pulmonary mucosa has a large surface area to provide good absorption and penetrability, polypeptide and protein drugs can be rapidly absorbed through pulmonary mucosa. This method can not only avoid the destruction or the metabolism of the polypeptide and protein drugs in the stomach and intestine, as well as the first-pass effect in the liver, but also increase the bioavailability of the drugs and improve the convenience for and compliance of the patients (Z. Shao et al., Pharm. Research, Vo. 11, No. 2, p. 243-250, 1994). Furthermore, the drugs can directly enter the major targeted organs so as to reduce the side effects generated by injection. Therefore, the pulmonary delivery has the most potential for polypeptide and protein drugs.

However, as stated by Patton et al. (Clin. Pharmacokinet, 2004: 43(12) 781-801), absorption enhancers in the pulmonary absorbed agents can improve the absorption of the drugs, but may also cause toxicity in the lung. For example, absorption enhancers may stimulate the increase of the eosinophil in the lung and result in an allergic reaction, or cause the increase of the neutrophil to induce acute inflammation in the lung. Even more, absorption enhancers may increase the production of LDH enzyme and/or the infiltration of proteins into the blood to cause toxic reactions or injuries in the pulmonary tissues and cells.

The present invention provides an aqueous inhalation pharmaceutical composition of a polypeptide or protein, which has improved bioavailability and reduced lung toxicity.

SUMMARY OF THE INVENTION

One object of the present invention is to provide an aqueous inhalation pharmaceutical composition, which can increase the absorption of polypeptides or proteins in the lung.

Another object of the present invention is to provide an aqueous inhalation pharmaceutical composition for treating diabetes.

DETAIL OF THE INVENTION

Figure 1:
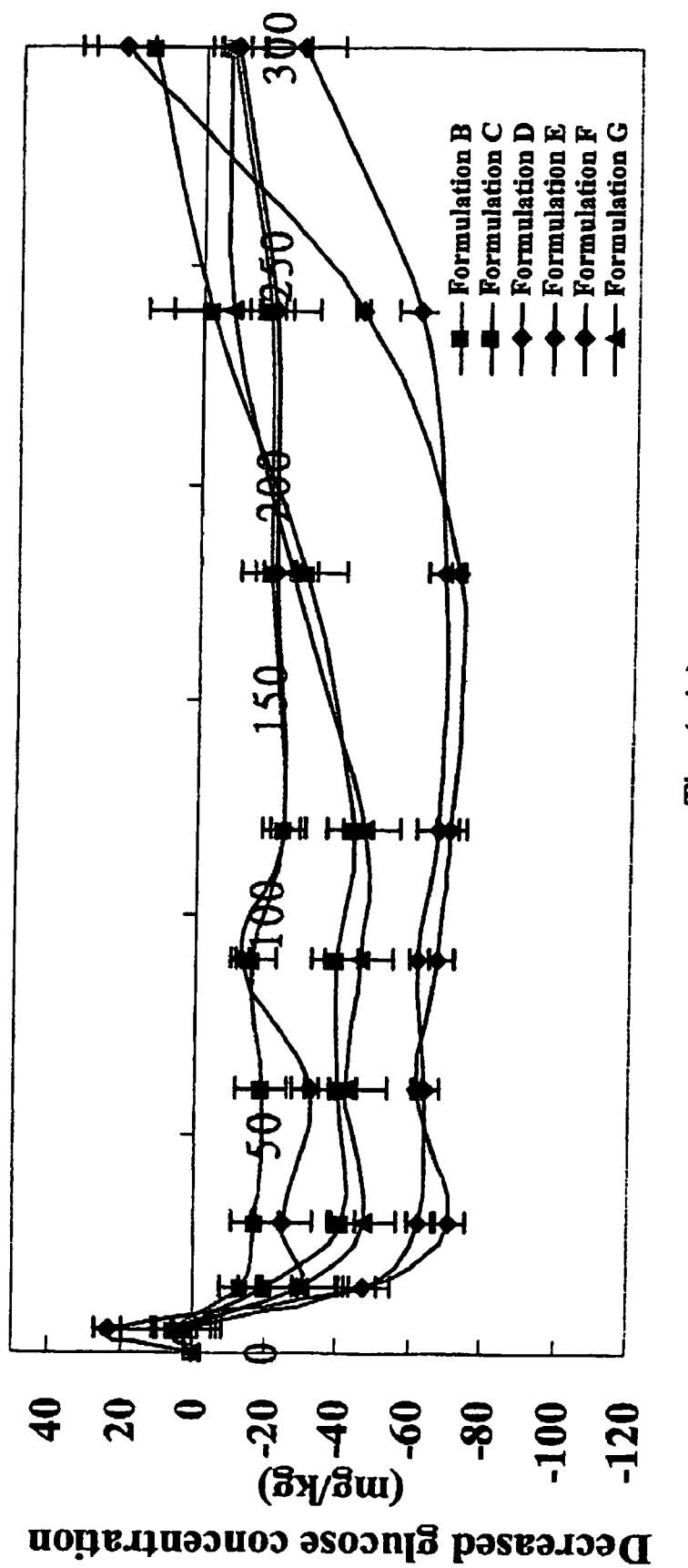
FIG. 1 shows the decreased concentration of glucose in the plasma of rats after they are administered with formulations B to G.

The aqueous inhalation pharmaceutical composition of the present invention comprises:
(i) a therapeutically effective amount of a polypeptide or protein;
(ii) an aqueous vehicle; and
(iii) an absorption enhancer selected from the group consisting of L-α-Lysophosphatidylcholine (LPTC) and derivatives thereof, and water-soluble surfactants.

The term "inhalation pharmaceutical composition" used herein represents a pharmaceutical composition which can be inhaled through the mouth or nose, and the active ingredient contained therein is absorbed via the lung.

The term "therapeutically effective amount" used herein represents the presented amount of the active ingredient that may cause an advantageous effect on a disorder in an individual in need of such treatment to alleviate or eliminate said disorder. When the disorder is diabetes, said term represents the amount which can effectively reduce the glucose level in the blood.

The terms "polypeptide" and "protein" used herein represent a polypeptide or protein having at least 10 natural or non-natural amino acid residues, preferably having from 20 to 60 natural or non-natural amino acid residues. Polypeptides and proteins suitable for the present invention include, but are not limited to, parathormone, parathormone antagonist, calcitonin, vasopressin, renin, prolactin, growth hormone, thyroid-stimulating hormone, corticotrophin, corticotrophin-releasing factor, follicle-stimulating hormone, corpus luteum hormone, Chorionic Gonadotrophin, atarial natriuretic peptide, interferon, tissue plasminogen activator, γ-globulin, factor VII, factor VIII, growth-hormone-releasing hormone, corpus luteum hormone-releasing hormone, growth hormone release-inhibiting factor, cholecystokinin, insulin, and analogues thereof, wherein insulin is preferred.

The term "insulin" used herein represents a natural or recombinant mammalian insulin (such as bovine, porcine, or human insulin). Human insulin is a protein comprising an A-chain having 20 amino acids and a B-chain having 20 amino acids, which are cross-linked by 3 disulfide bonds.

The term "analogue" used herein represents that one or more amino acids in the amino acid sequence of the polypeptide or protein are modified (such as being deleted and/or substituted) and/or one or more amino acids are inserted into the amino acid sequence of the polypeptide or protein. However, the modification and/or insertion do not substantially affect the activity of the polypeptide or protein.

The term "aqueous vehicle" used herein represents a water-contained vehicle that is capable of dissolving the active ingredients. The aqueous vehicle would not substantially affect the therapeutic effect of the active ingredients and would not cause undesired side effects on the treated subject. Aqueous vehicles suitable for the present invention include, but are not limited to, sodium chloride solution, dimethylsulfoxide, dimethylformamide, and polyol, wherein sodium chloride solution is preferred.

The composition of the present invention may further comprise one or more buffers. The buffer can be any conventional compound that is capable of effectively maintaining the pH of the composition in a desired range. The buffers suitable for the present invention include, but are not limited to, phosphate, acetate, citrate, TRIS, arginine, and histidine.

The composition of the present invention may further comprise one or more pH adjusters. Suitable pH adjusters for the present invention include, but are not limited to, hydrochloric acid, sodium hydroxide, lactic acid, tartaric acid, succinic acid, and a combination thereof.

The pH value of the composition of the present invention can be adjusted from about 2.0 to about 9.0 depending on the physicochemical properties of the active ingredient. The preferred pH value is from about 7.0 to about 8.0.

The term "absorption enhancer" used herein represents a compound that is capable of improving the absorption of the active ingredient via the lung. The absorption enhancer is compatible with the aqueous vehicle and would not cause undesired side effects on the treated subject.

According to the present invention, the absorption enhancer is selected from the group consisting of L-α-Lysophosphatidylcholine (LPTC) and derivatives thereof, and a water-soluble surfactant.

The term "L-α-Lysophosphatidylcholine (LPTC) derivative" used herein represents the LPTC substituted by an alkylcarbonyl having 6 to 20 carbon atoms, such as hexanoyl, octanoyl, lauroyl, myristoyl, palmityl, or stearoyl substituted LPTC.

The term "water-soluble surfactant" used herein represents any conventional anionic, cationic, amphionic and non-ionic surfactant, such as Tween-series surfactants, wherein Tween-20 and Tween-80 are more preferable, and Tween-80 is most preferable.

The osmotic pressure provided by the composition of the present invention is preferably from about 270 to about 330 mOsm/kg.

The amount of the polypeptide or protein in the composition of the present invention is from about 0.05 to about 20.0 mg/ml, preferably from about 1.0 to about 15.0 mg/ml, more preferably from about 1.0 to about 5.0 mg/ml.

The amount of the absorption enhancer in the composition of the present invention is from about 0.001 to about 10 mg/ml, preferably from about 0.01 to about 5 mg/ml, more preferably from about 0.1 to about 5.0 mg/ml.

The composition of the present invention can be administered by various conventional inhalation devices, such as liquid nebulizers and the like. Said inhalation device should be able to deliver small particles, such as the particles having a size of less than about 1 to about 10 μm of mass median aerodynamic diameter (MMAD), or less than about 1 to about 5 μm of MMAD, and preferably about 1 to about 3 μm. Inhalation devices suitable for conducting the present invention include, but are not limited to, the commercially available inhalation devices, such as Jet Nebulizer-Pulmo-Aide® 5650D (DEVILBISS®), Ultrasonic Nebulizer, Model NE520 (DEVILBISS®), Medisana® Ultra-S (MEDISANA®), Ultravent nebulizer (Mallinckrodt), Acorn II nebulizer (Marquest Medical Products), and Mesh Nebulizer (OMRON®), and those disclosed in WO 98/48873, WO 99/07340, US 2002/0124852 A1, US 20030064032 A1, and US2004/0089290.

The specific dose of the composition of the present invention can be determined and varied by the physician depending on the severity of the disorder, the properties of the composition, the potency of the polypeptide or protein, and the administration device. Generally, a subject in need of the treatment takes the dose for 1 to about 3 times every day, or optionally more times, to effectively treat the disorder.

The following embodiments are intended to further illustrate the present invention, and are not intended to limit the present invention. Any modification and application made by those of ordinary skill in the art based on the teachings of the specification are all within the scope of the present invention.

Example 1

Stability of Human Insulin at Different pH Values

Human insulin (Sigma, Lot 081K13562) was added into different buffer solutions of pH 3.0, 4.5, 6.0, 7.5, and 9.0, respectively, to formulate human insulin solutions having 1 mg/ml of human insulin. After filtering through a filter membrane (Supor Acrodisc 13), the initial concentration of human insulin in each solution was measured by using a High-Performance Liquid Chromatography (RP-HPLC). Each solution was allotted and capped in vials, and then the vials were stored at 4° C., 25° C., and 37° C., respectively. The residual amount of the human insulin in each vial was determined one month later. The results are shown in Table 1 below.

TABLE 1

|  | Initial concentration mg/ml | 4° C., one month | | 25° C., one month | | 37° C., one month | |
| --- | --- | --- | --- | --- | --- | --- | --- |
|  |  | mg/ml | Residual rate (%) | mg/ml | Residual rate (%) | mg/ml | Residual rate (%) |
| pH 3.0 | 0.9683 | 0.9609 | 99.24% | 0.5991 | 61.88% | 0.0919 | 9.49% |
| pH 4.5 | 0.5877 | 0.5603 | 95.34% | 0.5991 | 88.47% | 0.2582 | 43.94% |
| pH 6.0 | 0.0778 | 0.0824 | 105.95% | 0.0783 | 100.69% | 0.0676 | 86.89% |
| pH 7.5 | 1.0230 | 1.0397 | 101.62% | 1.0544 | 103.06% | 0.9741 | 95.22% |
| pH 9.0 | 0.0824 | 0.0881 | 106.94% | 0.0754 | 91.54% | 0.0558 | 67.76% |

According to the results of Table 1, it is found that the human insulin solutions are most stable at 4° C., less stable at 25° C., and least stable at 37° C. Furthermore, it is found that human insulin is most stable in the solutions of pH 7.5 and less stable at pH 6.0 and pH 9.0.

Example 2

In Vivo Bioavailability and Toxicology Studies of Pulmonary Absorption Enhancers 1. Formulations Formulation A: 50 mM phosphate, 100 mM NaCl, pH 7.5.

Formulation B: human insulin (5.0 IU/ml (0.2 mg/ml)), 50 mM phosphate, 100 mM NaCl, pH 7.5; final administered concentration of human insulin: 2 IU/kg (0.08 mg/kg).

Formulation C: human insulin (10.0 IU/ml (0.4 mg/ml)), 50 mM phosphate, 100 mM NaCl, pH 7.5; final administered concentration of human insulin: 4 IU/kg (0.16 mg/kg).

Formulation D: human insulin (10.0 IU/ml (0.4 mg/ml)), LPTC-lauroyl (L-LPTC; (1.0 mg/ml)), 50 mM phosphate, 100 mM NaCl, pH 7.5; final administered concentration of human insulin: 4 IU/kg (0.16 mg/kg).

Formulation E: human insulin (10.0 IU/ml (0.4 mg/ml)), LPTC-palmityl (P-LPTC; (0.5 mg/ml)), 50 mM phosphate, 100 mM NaCl, pH 7.5; final administered concentration of human insulin: 4 IU/kg (0.16 mg/kg).

Formulation F: human insulin (5.0 IU/ml (0.2 mg/ml)), LPTC-hexanoyl (C-LPTC; (0.5 mg/ml)), 50 mM phosphate, 100 mM NaCl, pH 7.5; final administered concentration of human insulin: 2 IU/kg (0.08 mg/kg).

Formulation G: human insulin (5.0 IU/ml (0.2 mg/ml)), Tween-80 (10 mg/ml), 50 mM phosphate, 100 mM NaCl, pH 7.5; final administered concentration of human insulin: 2 IU/kg (0.08 mg/kg).

2. Animal Model

Sprague-Dawley male rats weighted 200-250 g were randomly divided into 7 groups. According to the method disclosed in Enna, S. T. et al. (J. Physiol., 1972, 222: 409-414), after the rats were narcotized by abdominally injecting pentobarbital sodium (28.6 ml/kg), catheters were inserted into the trachea and the left femoral artery, respectively, from the cut neck. Group 1 was the control group, wherein each rat was administered with Formulation A only. The rats of Groups 2 and 3 were administered with Formulations B and C, respectively, which contain human insulin but without the absorption enhancer. The rats of Groups 4 to 7 were administered with Formulations D to G, respectively, which contain human insulin and the absorption enhancer.

After administering the formulations to the lung for 0, 5, 15, 30, 60, 90, 120, 180, 240, and 300 minutes, 0.25 ml of blood sample was collected from each rat. After the pulmonary administration for 5 hours, an excess amount of pentobarbital sodium (3 ml) was injected into the femoral artery of the rats. After 5 minutes, the rats were bled and then pulmonary perfusion with phosphate buffer solution was performed.

3. Determination of the Concentration of Insulin in the Plasma

The collected blood samples were centrifuged at 3000 rpm in 4° C. for 15 minutes. The upper layer of the plasma was collected. The concentrations of glucose in the upper layer samples of plasma were determined by the utilization of a blood sugar analyzer (YSI 2300 STAT PLUS, SMARTEC SCIENTIFIC CORP. Ltd.). The results are shown in FIG. 1. The concentrations of insulin in the upper layer samples of plasma were determined by the utilization of a Rat Insulin ELISA Kit (Mercodia), and the pharmacokinetic parameters of the absorption enhancers were further analyzed. The results are shown in Table 2.

4. Analysis of Total Protein and Lactate Dehydrogenase (LDH) in the Blood

The collected first 5 ml pulmonary perfusion samples were centrifuged at 350×g in 4° C. for 10 minutes. The supernatants were collected and further centrifuged at 14300×g in 4° C. for 30 minutes. The supernatants were collected for total protein and LDH analyses.

Based on the pigmentation principle of Biuret reaction (British Pharmacopoeia, p. A23 (1998)), the amount of total protein was determined by measuring the value of $OD_{546}$ with Autoanalyzer Hitachi 7150; then, the value was converted into the concentration of the protein (the results are shown in Table 3).

Based on the standard operation procedures of the GSCC (German Society of Clinical Chemistry; Recommendation of the German Society for Clinical Chemistry: Z. Klin. Chem. Klin. Biochem., 10, 287-288, 1972), the activity of LDH was determined by measuring the change of $OD_{340}$ with Autoanalyzer Hitachi 7150; then, the change was converted into the activity of LDH (the results are shown in Table 3).

5. Analysis of Total Account of Cell Number and Cell Differentiation

The collected second, third and fourth pulmonary perfusion samples were centrifuged at 350×g in 4° C. for 10 minutes. The precipitates were collected and combined with the precipitates collected from the centrifuged first pulmonary perfusion samples. Each precipitate was resuspended in a phosphate buffer solution (1 ml). The total account of cell number and the cell differentiation in each sample were automatically calculated and analyzed by an ADVIA 120 instrument (the results are shown in Table 3).

6. Results and Discussion

The relationship between the insulin dose and the reduction of blood sugar concentration in serum can be seen from the results of FIG. 1 and Table 2. It has been found that when the doses of insulin are 2 IU/kg (0.08 mg/kg) and 4 IU/kg (0.16 mg/kg), the averages of their area under the effect curve (AUEC) are 5207 mg/dl×min and 8281 mg/dl×min, respectively. Meanwhile, it can be found from the results of Table 2 that the bioavailability of insulin can be greatly increased by the addition of the absorption enhancers into the formulations. Particularly, the addition of Tween-80 shows a maximal increase of 84.6%.

The results of table 3 show that, except for LDH, all parameters including the total accounts of cell number, the percentages of macrophage, the percentages of neutrophil, the percentages of eosinophil, and the amounts of total protein obtained from the formulations are not substantially different statistically. Although the insulin formulations (with or without an absorption enhancer) may increase the activity LDH as compared to the control group without insulin, the differences of the activity of LDH between the formulations with an absorption enhancer and the formulations without an absorption enhancer are not statistically significant. This result proves that Tween-80 and L-LPTC would not induce toxic side effects in the lung.

TABLE 2

| | E peak (mg/dl) | T peak (min) | AUEC (mg/dl × min) | Bioavailability (%) |
|---|---|---|---|---|
| Formulation B | 35 ± 10 | 115 ± 61 | 5207 ± 2040 | 43.0% |
| Formulation C | 50 ± 10 | 69 ± 30 | 8281 ± 2640 | 34.2% |
| Formulation D, n = 5 | 74 ± 6 | 168 ± 78 | 17295 ± 1579 | 71.3% |
| Formulation E, n = 3 | 75 ± 2 | 80 ± 46 | 15387 ± 574 | 63.6% |
| Formulation F, n = 3 | 41 ± 3 | 35 ± 23 | 6160 ± 1394 | 50.9% |
| Formulation G, n = 7 | 55 ± 26 | 75 ± 48 | 10237 ± 7569 | 84.6% |

TABLE 3

| | Formulations | | | |
|---|---|---|---|---|
| Parameters | A (control group) (n = 6) | B (n = 6) | D (n = 6) | G (n = 4) |
| total account of cell number (cell/ml) × $10^6$ | 4.0 ± 1.80 | 4.03 ± 1.43 | 3.57 ± 1.59 | 3.01 ± 1.45 |
| macrophage % | 54.9 ± 7.52 | 63.8 ± 11.2 | 57.2 ± 5.43 | 56.7 ± 10.2 |
| neutrophil % | 44.8 ± 7.53 | 35.8 ± 11.1 | 42.0 ± 5.44 | 42.7 ± 10.2 |
| Eosinophil % | 0.32 ± 0.6 | 0.38 ± 0.14 | 0.76 ± 0.66 | 0.58 ± 0.09 |
| LDH | 111 ± 36.4 | 286 ± 190 | 309 ± 20.9 | 292 ± 158 |

TABLE 3-continued

| | Formulations | | | |
|---|---|---|---|---|
| Parameters | A (control group) (n = 6) | B (n = 6) | D (n = 6) | G (n = 4) |
| (mU/ml) Amount of total protein (mg/ml) | 0.00 ± 0.00 | 0.05 ± 0.12 | 0.15 ± 0.20 | 0.10 ± 0.15 |

We claim:

1. An aqueous inhalation pharmaceutical composition for treating diabetes, consisting of:
    (i) an insulin in a concentration of about 0.05 to about 20.0 mg/ml;
    (ii) an aqueous vehicle;
    (iii) Tween-80; and
    (iv) buffer for maintaining the value of pH;
    wherein said composition has an osmotic pressure of from about 270 to about 330 mOsm/kg.

2. The pharmaceutical composition according to claim 1, wherein the aqueous vehicle is sodium chloride solution.

3. An aqueous inhalation pharmaceutical composition consisting of:
    (i) an insulin in a concentration of about 0.05 to about 20.0 mg/ml;
    (ii) an aqueous vehicle;
    (iii) Tween-80; and
    (iv) pH adjuster;
    wherein said composition has an osmotic pressure of from about 270 to about 330 mOsm/kg.

4. The pharmaceutical composition according to claim 1, which has a pH from about 7.0 to about 8.0.

5. The pharmaceutical composition according to claim 1, wherein the amount of the insulin is from about 1.0 to about 5.0 mg/ml.

6. The pharmaceutical composition according to claim 1, wherein the content of Tween-80 is from about 0.001 to about 10 mg/ml.

7. The pharmaceutical composition according to claim 3, wherein the aqueous vehicle is sodium chloride solution.

8. The pharmaceutical composition according to claim 3, which has a pH from about 7.0 to about 8.0.

9. The pharmaceutical composition according to claim 3, wherein the amount of the insulin is from about 1.0 to about 5.0 mg/ml.

10. The pharmaceutical composition according to claim 3, wherein the content of Tween-80 is from about 0.001 to about 10 mg/ml.

* * * * *